(12) United States Patent
McGill et al.

(10) Patent No.: US 8,101,915 B2
(45) Date of Patent: Jan. 24, 2012

(54) DETECTION OF CHEMICALS WITH INFRARED LIGHT

(75) Inventors: R Andrew McGill, Lorton, VA (US);
Chris Kendziora, Burke, VA (US);
Robert Furstenberg, Largo, MD (US);
Michael Papantonakis, Washington, DC (US); James S Horwitz, Fairfax, VA (US); Graham K Hubler, Highland, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 594 days.

(21) Appl. No.: 12/255,103

(22) Filed: Oct. 21, 2008

(65) Prior Publication Data

US 2010/0044570 A1    Feb. 25, 2010

Related U.S. Application Data

(60) Provisional application No. 61/135,531, filed on Oct. 24, 2007.

(51) Int. Cl.
*G01N 21/00* (2006.01)
(52) U.S. Cl. .................................................. 250/338.5
(58) Field of Classification Search .......... 250/330–335, 250/336.1–336.2, 338.1–338.5, 339.01–339.15, 250/340, 341.1–341.8
See application file for complete search history.

(56) References Cited

U.S. PATENT DOCUMENTS

| 6,797,944 | B2 | 9/2004 | Nguyen et al. |
| 6,828,795 | B2 | 12/2004 | Krasnobaev et al. |
| 6,984,524 | B2 | 1/2006 | Nguyen et al. |
| 6,995,846 | B2 * | 2/2006 | Kalayeh et al. ............... 356/437 |
| 6,998,156 | B2 | 2/2006 | Bubb et al. |
| 7,262,414 | B1 | 8/2007 | Carrieri et al. |
| 2002/0166969 | A1 * | 11/2002 | Chou et al. ............... 250/339.08 |
| 2006/0023211 | A1 * | 2/2006 | Gandhi et al. ................ 356/318 |
| 2008/0185525 | A1 * | 8/2008 | Lyubchik et al. ............. 250/342 |

OTHER PUBLICATIONS

Geiger et al., "Mid-infrared mutli-wavelength source for lidar applications," 1998, SPIE Proceedings, vol. 3380, pp. 63-69.*
Winter et al., "Detection of extended targets using multi-spectral infrared," 1993, SPIE Proceedings, vol. 1954, pp. 173-180.*
Prasad et al., "Tunable IR differential absorption lidar for remote sensing of chemicals,", 1999, SPIE Proceedings, vol. 3757, pp. 87-95.*

(Continued)

*Primary Examiner* — Kiho Kim
(74) *Attorney, Agent, or Firm* — Amy L. Ressing; Rebecca L. Forman (57) ABSTRACT

The present invention is directed to a method for non-contact or stand off chemical detection by selectively exciting one or more analytes of interest using an IR source tuned to at least one specific absorption band without significantly decomposing the analyte and determining if the analyte is present by comparing emitted photons with an IR detector signal made before and during or shortly after exciting the analyte. Another embodiment provides a method for non-contact or stand off chemical detection by selectively exciting one or more analytes of interest using an IR source tuned to at least one specific absorption band without significantly decomposing the analyte, wherein the analyte is excited sufficiently to generate a vapor plume, and wherein the plume is examined to detect the presence of the analyte. Additionally, the present invention provides for a system for non-contact or stand off chemical detection.

46 Claims, 11 Drawing Sheets

OTHER PUBLICATIONS

Pasmanik et al. "Development of eyesafe IR lidar emitter and detector technologies," 1997, SPIE Proceedings, vol. 3065, pp. 286-293.*
Vaicikauskas et al., "Infrared DIAL system for remote sensing of hazardous chemical agents," 2004, SPIE Proceedings, vol. 5613, pp. 21-28.*
Tittel et al., "Chemical sensors based on quantum cascade lasers," SPIE Proceedings, vol. 4817, pp. 8-13.*
Prarad et al., "Portable Digital lidar—a Compact stand-off bioagent aerosol sensor," 2001, SPIE Proceedings, vol. 4378, pp. 50-59.*
Stevens et al., "Remote chemical sensing by laser optical pumping," 1996, SPIE Proceedings, vol. 2833, pp. 80-93.*
Quagliano et al., "Spectroscopic analysis of infrared DIAL measurements," 1995, SPIE Proceedings, vol. 2702, pp. 16-27.*
Harper et al., "Remote chemical sensing with quantum cascade lasers,", 2004, SPIE Proceedings, vol. 5403, pp. 378-386.*
Petryk, Michael W. P., "Promising Spectroscopic Techniques for the Portable Detection of Condensed-Phase Contaminants on Surfaces", Applied Spectroscopy Reviews, 42:3, 287-343 (2007).

* cited by examiner

DETECTION OF CHEMICALS WITH INFRARED LIGHT

PRIORITY CLAIM

The present application claims priority from U.S. Provisional Application No. 61/135,531 filed on Oct. 24, 2007 by R. Andrew McGill et al., entitled "Method of Chemical or Biochemical Detection," the entire contents of which are incorporated herein by reference.

BACKGROUND OF THE INVENTION

1. Field of the Invention

The present invention relates generally to chemical or biochemical detection and more specifically to molecular or ion detection by selective thermal heating with incident infrared light resonant with one or more selected infrared absorption bands, and examination of vapor or light produced as a result of said incident light.

2. Description of the Prior Art

Low vapor pressure analytes, in their condensed physical state, such as explosives, drugs of abuse, and chemical warfare agents, are difficult to detect in a non contact or stand off mode, using conventional technology. Since the handling of these materials leaves persistent trace contaminations on contacted surfaces (e.g., door handles, pockets, hands, containers, etc.), manual swipes are often used to lift particles or residue of the analytes for subsequent analysis, for example in airport hand luggage screening. However, performing a manual swipe of each potential suspect and container is often impractical or inconvenient, and it inhibits covert detection.

A summary of existing and emerging technologies for the portable detection of contaminants, such as chemical warfare agents, is outlined by Michael W. P. Petryk in his article entitled "Promising Spectroscopic Techniques for the Portable Detection of Condensed-Phase Contaminants on Surfaces," found in *Applied Spectroscopy Reviews*, 42: 287-343, 2007, the entire contents of which are incorporated herein by reference. Moreover, U.S. Pat. No. 6,998,156 to Bubb et al. describes using an infrared laser to vaporize target material. The entire contents of the Bubb patent are incorporated herein by reference.

For trace detection of explosives or drugs, the current technologies typically work well as long as particles can be collected by some physical means and then thermally converted into vapor for analysis or detection. The sampling techniques use non-selective removal of particles from a selected few surfaces which may have been contaminated with particles of explosives and transfer them onto a heated surface which is interfaced to an ion mobility spectrometer (IMS) or other explosive detection system (EDS). Previously, this has required either a physical rubbing process or forced air removal, neither of which is material selective or practical for any significant stand off distance and can add a significant time and personnel cost burden to the detection process. In addition, the efficiency of physical removal of particles from a surface as particles depends on the techniques used, the training level of the person removing the particles, and the rubbing or contaminated surface material or surface roughness of contaminated surfaces.

Known methods of heating trace samples of explosives for detection purposes include broad band IR sources which heat in a non selective fashion. This approach consumes much more power than a selective heating process and generally heats everything incident with the heating source. This increases the general background level in the vapor phase of all the volatile chemicals in the material examined and can result in an increase in signal clutter or false alarms, especially when the substrate materials or additional contaminants being examined are of a complex natural origin such as leather, wood or food products.

Laser induced breakdown spectroscopy (LIBS) is an alternative laser based technique but this requires significantly higher power and results in the destruction of the sample of interest and the surface on which it directly resides. The lasers used for LIBS are typically high power (10 mJ or greater) with short wavelengths (UV to near IR) and are not considered safe for environments where humans might be exposed or for the integrity of the substrate being examined. LIBS is a type of atomic emission spectroscopy which utilizes a highly energetic laser pulse as the excitation source to ablate material, reducing it to its elemental constituents. LIBS can analyze any matter regardless of its physical state, be it solid, liquid or gas. Because LIBS detects elements, its selectivity in the presence of many materials is suspect and is reliant on signal ratios of elements which can be confused when mixtures of materials are present. Nitrogen, for example, is present in many explosives but it is also prevalent in cotton or wool fiber or any proteinacous material. Trace explosives present on natural fibers would be difficult to detect accurately with LIBS.

Raman spectroscopy is an emerging standard for optical identification and characterization of known and unknown samples. It couples to signature vibrational modes of the analyte and is complementary to infrared spectroscopy. Its main drawback is in its inefficiency because typically only one photon is Raman scattered for every million photons incident on the sample. Furthermore, Raman is isotropic, meaning there is no preferred direction for the scattered light to travel. This limits its application for stand off detection. For a fixed collection optic diameter, the photon collection efficiency decreases proportional to the second power of the distance to the sample under interrogation. Finally, Raman efficiency is optimized with high photon energy light which is not eye-safe to use in the presence of people.

Photo-thermal spectroscopy is another potential tool that is used in stand-off detection. In this technique, the sample is heated with a non-resonant, not eye-safe laser (usually visible wavelength of near-IR) in a periodic fashion (using a mechanical chopper). The detected signal consists of the amplitude of the heated signal measured by an IR detector (or some other means) and its phase-angle shift with respect to laser heating. This method differs from the present invention, in part, because it does not take advantage of the resonant nature of absorption of IR radiation which allows analyte selectivity right at the excitation stage and with much less laser power to achieve suitable heating.

One method of detecting explosives uses a broadband heating source connected to an IMS. One problem with this method is that the entire composition of the surface, and possibly deeper, is heated which makes accurate detection of the analyte more difficult. Another method of detecting explosives, narcotics and other chemical substances, uses a laser source to ablate the particles, then collects them and subsequently analyzes them. Unfortunately, the ablation process may damage the analyte, resulting in additional signal clutter and possible reduction in the principle analyte signal, and this method requires a separate collection step.

BRIEF SUMMARY OF THE INVENTION

The aforementioned problems are overcome in the present invention which provides a method for non-contact or stand off chemical detection that may be eye-safe by selectively exciting one or more analytes of interest using an IR source tuned to at least one specific absorption band without significantly decomposing the analyte and determining if the analyte is present by comparing emitted photons with an IR detector signal made before and during or shortly after exciting the analyte. Another embodiment of the present invention provides a method for non-contact or stand off chemical detection that may be eye-safe by selectively exciting one or more analytes of interest using an IR source tuned to at least one specific absorption band without significantly decomposing the analyte, wherein the analyte is excited sufficiently to generate a vapor plume, and wherein the plume is examined to detect the presence of the analyte. The analyte of interest may be an explosive, an additive to an explosive, a drug, a chemical warfare agent, a biochemical, or a biological warfare agent. Additionally, the present invention provides for a system for non-contact or stand off chemical detection that may be operated in an eye-safe manner.

The present invention has many advantages over the prior art. It may detect at stand off distances and be safely pointed at targets in areas with people present. It may selectively target materials in a complex matrix. It may simultaneously detect a range of materials (e.g., explosives, drugs, and chemical agents). It may detect at video frame rates or faster. It may be hand held. It may be operated without the persons present being cognizant of the ongoing detection process. It may efficiently vaporize or probe particles that are embedded in a surface such that they are difficult to remove using the normal physical rubbing or particle removal techniques.

For the stand-off detection of explosives and devices such as IEDs, photonic detection has several inherent advantages compared to other methods. These advantages include: an extremely high detection speed, zero interference with the existing radar and communication systems, and the potential for long range stand-off sensing. While several other all-optical techniques such as LIBS and Raman have been proposed for stand-off detection, these suffer from the fact that the wavelengths and intensities required are not safe to eyes and skin, or even to surfaces examined such as painted automobiles.

By using more than one laser (multispectral mode) or even a continuously tunable laser (hyperspectral mode) further selectivity can be achieved by using a combination of resonant and/or non-resonant excitation. On the collection side, further selectivity can be achieved by detecting only portions of the thermal band that is characteristic to the analyte of interest. Furthermore, the present invention uses laser sources (e.g. QCLs) that are small, provide light that is invisible and safe to the human eye and are conducive to implementation in hand-held devices. Also, the transient response of the analyte to laser heating is measured instead of a response to periodic heating, thus providing a means for rapid detection as well as circumventing the problems associated with detection of loose powders/particles (such as explosives particulate residues) that are hard to detect using photothermal imaging due to long thermal constants. Also, the use of resonant infrared laser sources when properly focused to a small spot (to increase laser irradiance) can cause the analyte to partially or completely vaporize and be detected by sophisticated IMS detectors or other suitable vapor detectors which may be optically based and probe the vapor generated in concert with the vaporization process to allow interrogation during the time period where the concentration of vapor is high, before the vapor diffuses or moves by other means to a lower concentration condition. This embodiment of the present invention may be non-contact or stand-off, and provides advantages over currently available detection methods, especially compared to contact techniques that involve physical rubbing or air jetting of the substrate to remove solid particles of material to examine.

These and other features and advantages of the invention, as well as the invention itself, will become better understood by reference to the following detailed description, appended claims, and accompanying drawings.

BRIEF DESCRIPTION OF THE DRAWINGS

FIG. 8 shows thermal images of RDX deposited as a trace quantity on a gold mirror substrate illuminated with a QCL with 5 mW/mm$^2$ incident light at 6.3 microns. FIG. 8(a) is an image with the laser off, 8(b) is an image with the laser on, and 8(c) is a differential image which clearly defines the RDX location and spatial distribution in the center.

DETAILED DESCRIPTION OF THE INVENTION

According to the present invention, low vapor pressure analytes (e.g., explosives, additives to explosives, drugs, chemical warfare agents, biochemicals, and biological warfare agents) that are typically present as solid particles or as a thin film residue under ambient conditions can be detected at non contact or stand off distances. After someone handles illicit materials, particles of explosives or drugs are unwittingly transferred through fingerprints onto objects and surfaces that the person touches, or after a release of a chemical agent, the disseminated chemical is distributed onto a variety of surfaces as a trace residue. The contaminated object or surface can be excited (e.g., heated) actively and selectively by using an IR laser or a filtered light source so that a narrow wavelength range is used to be resonant with one or more selected absorption band(s) of the analyte of interest. Selective heating is used to maximize heating of the analyte of interest and to minimize heating or potential damage to materials that are not of interest to the detection application (e.g., substrate, contaminants), with the added benefit that significantly less laser power is needed. The laser is coupled in a resonant fashion to one or more selected infrared absorption band(s), with a wavelength between 1 and 20 microns, to maximize the efficiency of energy transfer and to avoid electronically excited states that commonly lead to decomposition products. Typically, by selectively exciting the analyte using an IR source tuned to a specific absorption band, no more than five percent of the analyte is decomposed.

Detecting the analyte of interest may be accomplished by using any appropriate analytical tool. Examples include examining thermal or photo emissions with an IR detector and examining a vapor plume generated by the heating. Using thermal or photo emissions, signals, such as images, of a given object or surface are used to detect the analyte of interest. An image taken before heating is compared to an image during heating. The difference between the images or a differential image created by subtracting the image taken before from the image taken during heating can identify the presence of the analyte of interest. When sufficient laser energy is used to generate a significant amount of vapor, the vapor plume can be analyzed by various optical means that are separate from the original IR heating source. This could be achieved via a light absorption phenomena or LIDAR or cavity-ringdown techniques. Alternatively, the generated vapor plume could be analyzed by an instrument like an IMS or a technique like gas chromatography.

Figure 1:
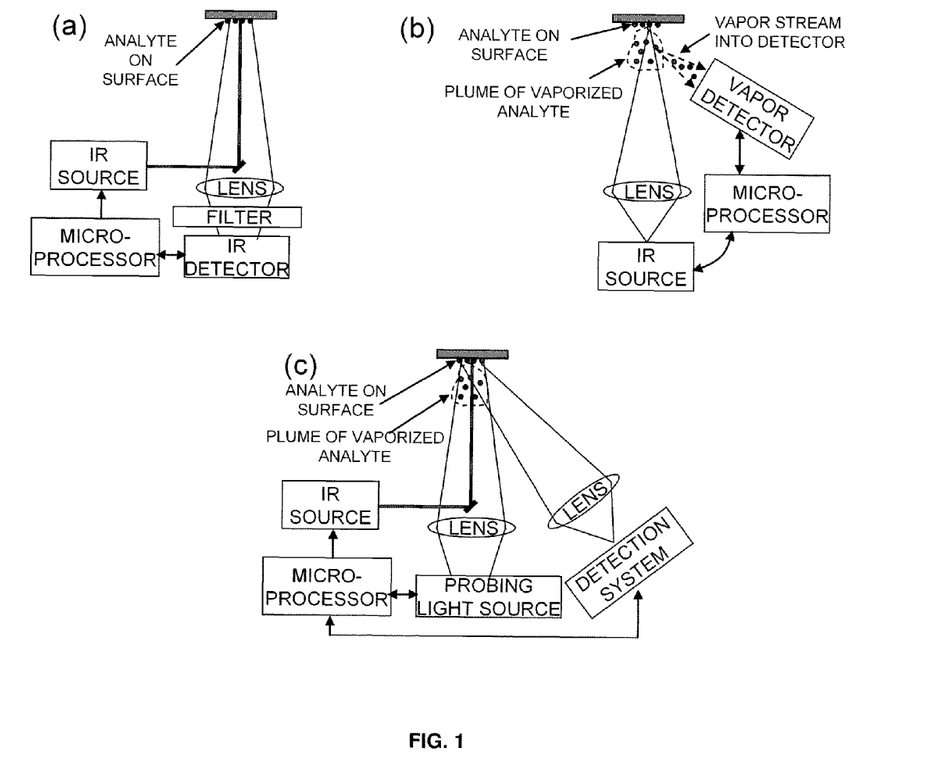
FIG. 1 is a schematic for three embodiments of the present invention: (a) shows detection using an IR source and an IR detector; (b) shows detection using an IR source and a vapor detector; and (c) shows detection using an IR source, a probing light source, and a detection system.

FIG. 1 shows a schematic for three embodiments of the present invention. FIG. 1(a) shows detection using an IR source and an IR detector. FIG. 1(b) shows detection using an IR source and a vapor detector. FIG. 1(c) shows detection using an IR source, a probing light source, and an optical detection system.

Figure 2:
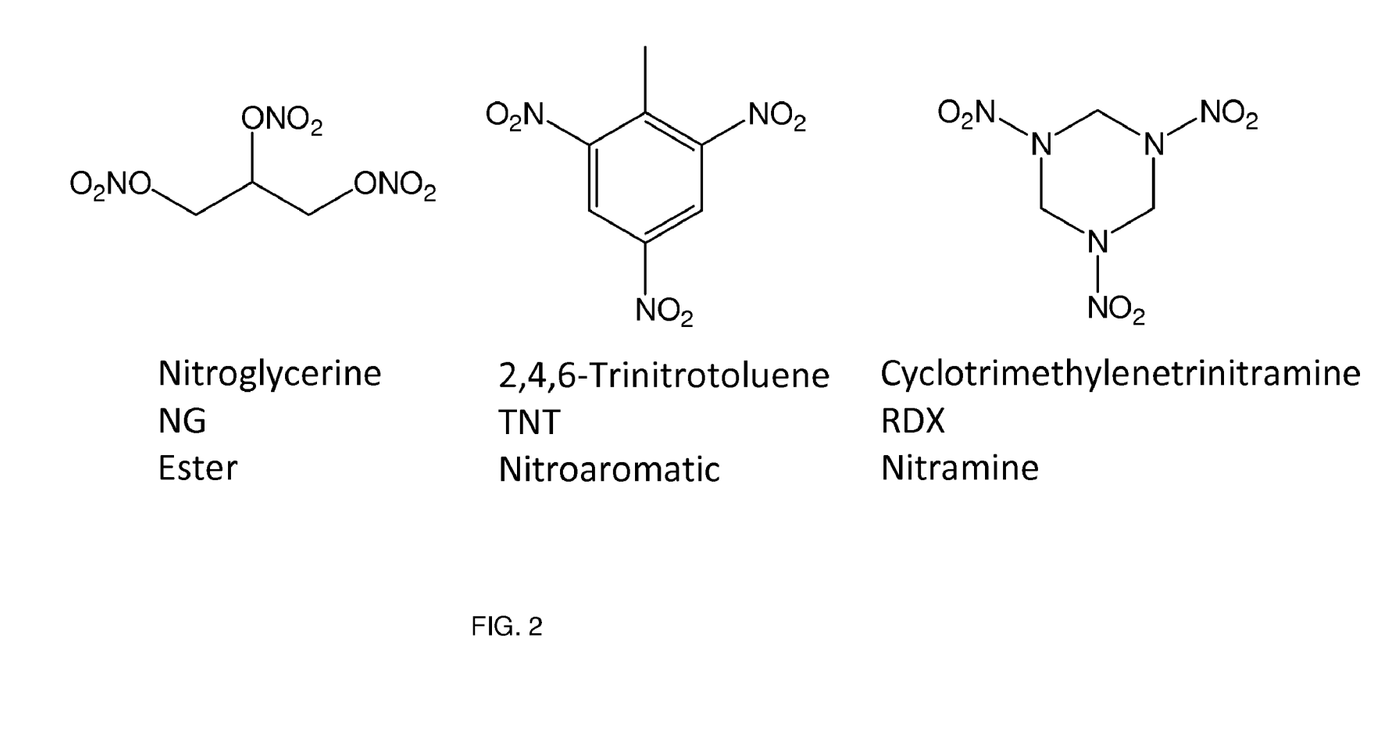
FIG. 2 shows the chemical structure of nitroglycerine, 2,4,6-Trinitrotoluene (TNT), and RDX.

The present invention provides a means to detect low vapor pressure analytes, such as explosives, drugs, and chemical agents, based on resonant absorption of certain infrared (IR) wavelengths. Some examples of explosives or components of explosives that may be detected include 24DNT, TNT, RDX, HMX, TETRYL, PETN, NG, EGDN, DMNB, ammonium nitrate, urea nitrate, ANFO, TATP, and $H_2O_2$. Some examples of drugs that may be detected include heroin, cocaine, barbiturates, LSD, and cannabis. Some examples of chemical agents that may be detected include nerve (G), blister (H), blood, incapacitating, and lacrymator. This system can be applied to virtually any material, including any explosive type, including organic or inorganic (ionic) explosives that cover the traditional (e.g. TNT, RDX, PETN, and ANFO) and non traditional materials (e.g. triacetonetriperoxide or TATP and $H_2O_2$) solid or liquid states, and it can be used to simultaneously detect all organic energetic materials probed at a common wavelength and containing the nitrogen-oxygen bond (N—O), which is in the majority of the commonly used explosives (see FIG. 2). Likewise, for the inorganic nitrates and peroxide based explosives, the system can be tuned to a wavelength at or near a peak in the absorption spectrum characteristic of the nitrate ion and peroxide structures respectively. To detect the class A drugs, the IR source can be tuned to a wavelength at or near a peak in the absorption spectrum characteristic of the carbon-nitrogen bond. In addition to low vapor pressure analytes, the present invention is also capable of detecting higher vapor pressure analytes.

Figure 3:
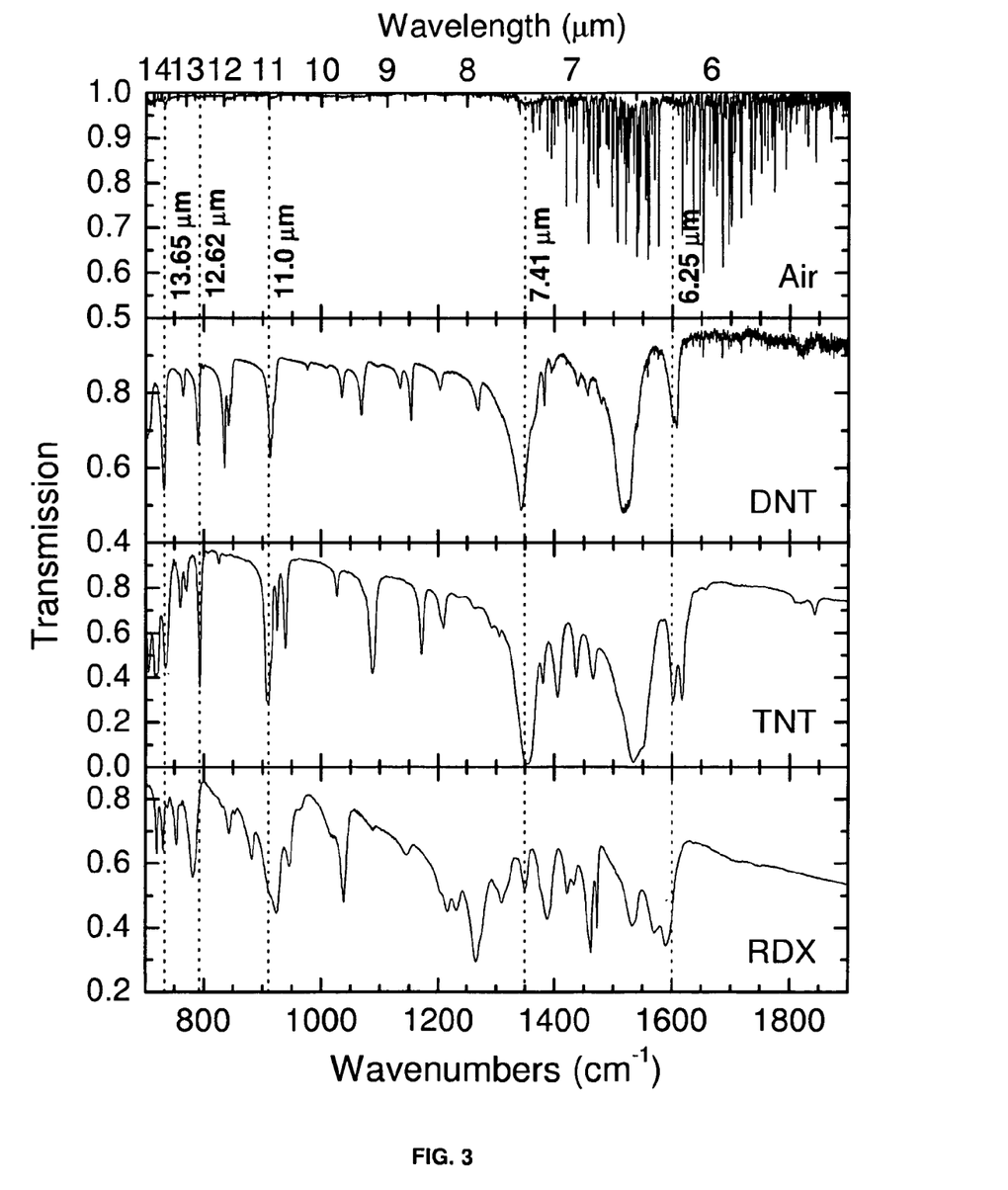
FIG. 3 shows IR transmission spectra of humid air, 2,4-dinitrotoluene (24DNT), TNT, and RDX. The N—O absorption stretching mode at 1600 cm$^{-1}$ (6.25 microns) falls in a fortuitous transparent window for air. Also highlighted are shared absorption bands at 7.41 μm, 11.0 μm, 12.62 μm and 13.65 μm that fall in an extended air transparency window.
Figure 4:
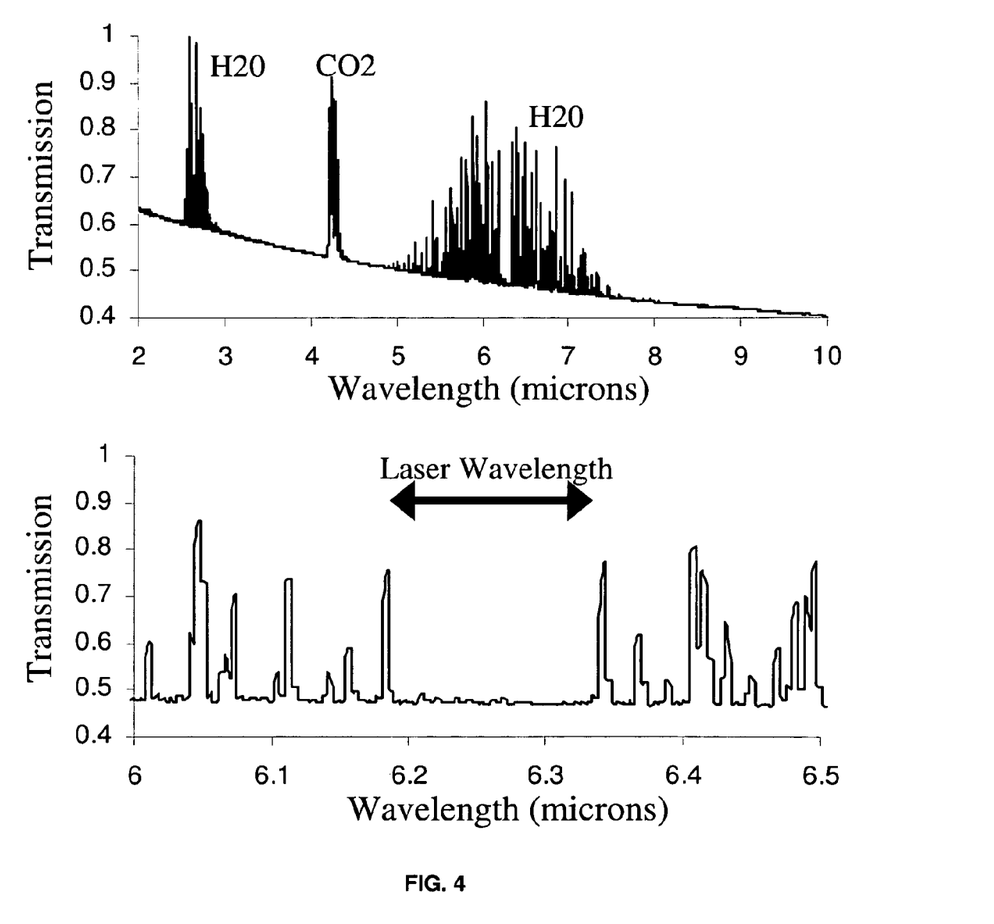
FIG. 4 shows the IR spectral absorbance properties of humidified air.

The N—O band in the nitro group has natural resonance frequencies (symmetric and anti-symmetric) in the mid and long IR wavelengths. The transmission spectra of organic based 24DNT, TNT and RDX chemicals shows that they exhibit a common absorption band near 6.25 μm as shown in FIG. 3. This N—O stretch band and several others fortuitously fall in transmission windows of air (see FIG. 4), making them suitable for in air stand-off detection applications.

Because the vapor pressures of the majority of explosives are very low and typically well below a few parts per trillion at room temperature, traditional optical stand-off detection techniques applied to plumes of industrial chemicals or chemical agents are largely not useful. Additionally, the vapor pressure of explosives can be significantly reduced in composites containing explosives, such as C4, and masked due to complex packaging. However, the surface contamination of explosives and this persistence in the solid state can be exploited for stand-off or non-contact detection by irradiating the explosive sample with one or more of the resonant absorption wavelengths highlighted in FIG. 3. At these wavelengths, the coupling efficiency of the optical energy can be 1000 times greater than if the wavelength were just a few $cm^{-1}$ away. Targeting any of these absorption peaks enables rapid, selective heating of the explosive material.

As the temperature of an object increases, the amount of IR radiation it emits increases, which allows IR imaging to map out local temperature changes. Industrial, medical, and military applications make use of this technology, and, because of good atmospheric transmission at some wavelengths, remote imaging is also possible. A trace amount of explosive residue, when illuminated at a resonant IR absorption wavelength, will heat up locally and is observable by an IR camera.

If the thermal properties of the substrate on which the analyte is found are known, then the knowledge of both the degree of heating and the cooling time can be used as inputs in an alarm algorithm. For example, more heating at selected wavelengths on a metallic substrate such as a door knob (fast cooling) carries more weight (i.e. more likely to contain explosive residue) in an alarm algorithm than the same amount of heating on a plastic or fibrous substrate (slow cooling).

Under one embodiment of the present invention, IR thermal imaging of a given scene is enhanced by illumination with an IR pulse (outside the camera detection wavelength range) to resonantly interact with the analyte or analytes of interest. By comparing images with the laser off to images with the laser on at video frame rates, a differential image with high fidelity can be generated which will distinctly identify explosive residue.

The resonant IR absorption wavelengths to use for heating should be common to explosives, but otherwise rare among possible substrate materials such as cotton, paper, plastics, metals etc. Further, by utilizing additional IR wavelengths, tests can be performed to probe for other types or classes of explosives as well as to increase system selectivity to confirm the type of explosive. In general, this approach offers advantages over other optical techniques in that it is eye-safe and compact.

Thermal imaging is enhanced by the heating signature due to the resonant absorption within the explosive residues of interest. For this embodiment, powerful mid-IR laser sources and sensitive IR focal plane arrays may be used. Both of these are commercially available today and should offer increased performance in upcoming years.

The IR source may be any source known in the art, such as a pulsed laser, continuous laser, broad band light source, filtered broad band light source, swept source, chirped source, variable source, or tunable source. Preferably, a quantum cascade laser (QCL), may be used as the IR photon source. The advantages of using QCL include: It can provide a single wavelength output allowing for the targeting of specific functional groups. It can operate at room temperature, and current devices can provide up to 1 Watt CW output, and it is commercially available. Moreover, a pulse is preferred over continuous wave (CW) for higher peak power, lower laser on times, and reduced cooling requirements. It is a stable laser source which in normal operation requires no consumable materials. It is microfabricated from semiconductor wafers to generate die, in mass production, with high yield, low cost and high quality. The inexpensive and miniature nature of the QCL die are attractive for the development of hand held instrumentation. At present, $\lambda$=6 µm QCLs have been demonstrated in continuous wave (CW) mode up to T=340 K (63° C.). The device can output 640 mW CW at room temperature and greater than 1.6 Watts when cooled to 100 K. These output powers in a laser tunable to the absorption bands of explosives makes the QCL an enabling technology for compact detectors used in non contact or stand off vaporization and detection of explosives.

Any thermal imaging hardware may be used. For example, an IR camera (such as a commercial FLIR camera) can be used to collect and analyze longwave infrared (LWIR) light. The advantages of this hardware include: it is a microfabricated bolometer thermal imaging array, it is uncooled for low power operation, it responds to the 7-12 µm band which includes wavelengths generated from thermal heating, and it is small and lightweight. Moreover, a telescopic lens may be used to increase stand off distance capability.

The IR detector may be a single channel or a multi channel detector. Also, the light entering the IR detector may be filtered to be selective for the analyte of interest.

In accordance with Kirchhoff's law, the thermal emission spectra of analytes correlate with their absorption spectra. To take advantage of the increased emissivity levels at absorption peaks in the thermal band where the detection occurs, a suitable optical filter can be designed which passes these analyte specific wavelengths and blocks all others. This way, only a signal attributable to the analyte is collected and the signal-to-noise ratio is increased. By combining both selective excitation and selective collection, the detection limit and detection selectivity of a given analyte can be greatly increased.

If there is sufficient IR light to generate a vapor plume, an optical technique may be used to examine said plume. The vapor may be examined using an IR source, visible source, UV source, IR detector, visible detector, UV detector, diffraction grating, filter wheel, Michelson interferometer, laser cavity, integrating sphere, or any other suitable equipment. The presence of the analyte may be determined by using IR absorption, IR backscattering, IR thermal luminescence, Raman spectroscopy, LIBS, or any other suitable technique.

If a vapor plume is generated, it can be detected by any means of vapor detection currently available or yet to be discovered. These include ion mobility spectrometry, mass spectrometry, gas chromatography, chemiluminescence, surface acoustic wave, gravimetric, microbalance, or crystal resonance.

The present invention can be inherently eye-safe, with anticipated IR irradiances that are far below the maximum permissible exposure limit, which is of the order of 100 $mW/cm^2$. As such, many uses can be envisioned for this system, such as to not only scan suspected IEDs, but also to scan people (including for example: clothing, skin, glasses, shoes, hat, hair), airline boarding passes, vehicles, luggage, parcels, etc. Anything that a person handling explosives contacts is a suitable target.

Two or more lasers may be used to increase sensitivity and selectivity or expand the range of analytes examined. Multiple lasers used in on- and off-resonance modes would improve the selectivity of the system by removing false positives which may occur because sometimes broadband absorbers heat independent of wavelength. Looking at the difference between the signals for on- and off-resonance with neighboring wavelengths will help remove effects from materials which are broad band IR absorbers and prevent false positives. If the difference between the two differential signals is negligible, the analyte of interest is concluded to be not present. To compare the difference between signals on- and off-resonance, compare either the difference of the differential signals or just the difference between the on- and off-resonance raw signals. The nature of the algorithm applied depends on the substrate material being examined.

The present invention is applicable in mobile and static applications. For mobile applications, the laser may be trained on a target so that as the detector/laser is moved the laser and camera remains trained on the target of interest. For targets which are mobile a static or mobile laser and camera can similarly be trained on the target of interest.

Another alternative is to use single element photo-conductive infrared detectors (such as mercury-cadmium-telluride). The advantage of this alternative is higher sensitivity (allowing longer stand-off distances), increased detector speed (allowing faster moving objects to be scanned) and incorporation of a less expensive detector. Also, higher detector speeds will allow the probing of the thermal pulse immediately after resonant heating (sub millisecond range) before the heat is transferred to the substrate (so called thermal luminescence regime), thus further decreasing the contribution of the substrate on the total thermal signature. This approach is likely to include a visible-light camera or visible optic with a cross-hair reference in the user interface for aiming the instrument at the desired measurement target.

Example 1

Figure 5:
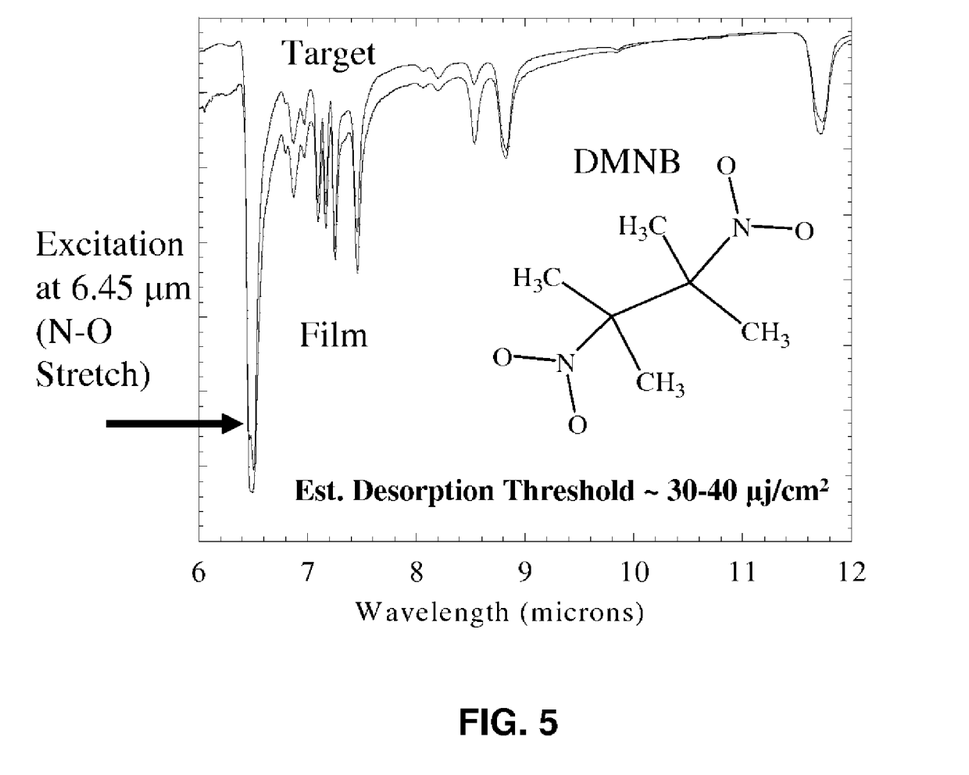
FIG. 5 shows an infrared spectrum for 2,3-dimethyl-2,3-dinitrobutane (DMNB) vaporized with an IR laser coupling to the N—O stretch. The IR laser tuned to 6.45 microns instantly evaporated the DMNB, and the collected material was shown to be essentially spectrally identical to the starting material.

A small sample of dimethylnitrobutane (DMNB) was positioned in a recessed stainless steel support inside a chamber under reduced pressure and positioned in line with a laser beam tuned to 6.45 microns. DMNB is a taggant that is added to formulation of explosives and has the same functional groups as some conventional explosives. It was selected for this experiment as a simulant or surrogate for an actual explosive but with very similar spectral properties. The laser used was a tunable free-electron laser that allows the user to select a wide range of wavelengths. The operational characteristics of the laser were as follows: wavelength of 6.45 microns, 6 microsecond pulse train of 1 ps pulses at 2.8 GHz, energy density of 30-40 micro J/cm$^2$ Immediately after directing the laser beam onto the DMNB target a visible plume of material was ejected. Some of this material was collected on a neighboring substrate for characterization by FTIR. As shown in FIG. 5, the collected material had the same spectral signature as the starting DMNB target material, proving that the laser energy was coupled into the DMNB without any significant chemical degradation. From a visual examination of the plume and the topography of the collected material, both vapor and particulate matter were ejected from the DMNB target. The laser intensity required to achieve these results was 30-40 microJ/cm$^2$.

Example 2

A small intrinsic sample of 2,4-dinitrotoluene (24DNT) positioned on a test surface under ambient laboratory conditions was exposed to a laser beam tuned to 6.25 microns. 24DNT is a natural degradation product of and an impurity in TNT that is structurally very similar to TNT with one less nitro group. It was selected for this experiment as a close surrogate for TNT with very similar spectral properties which was desirable for the intended tests. The laser used was a tunable free-electron laser that allows the user to select a wide range of wavelengths.

Figure 6:
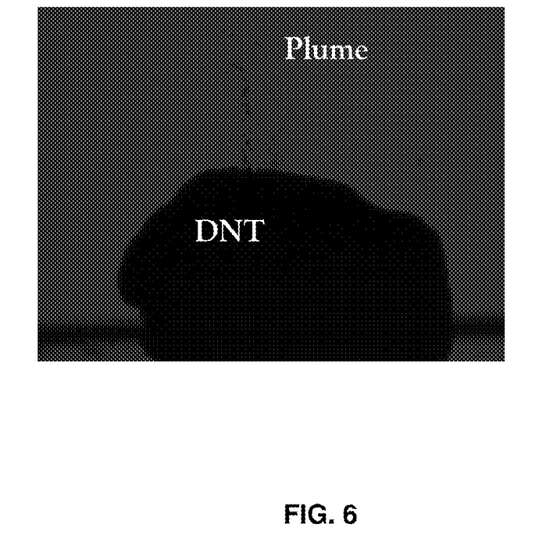
FIG. 6 shows a stroboscopic back-illuminated photo of a solid piece of 24DNT directly after exposure to a laser beam tuned to 6.25 microns. The vaporized 24DNT is clearly visible as a plume above the solid 24DNT 14 milliseconds after the laser pulse. Spectroscopic examination of 24DNT before and 24DNT after vaporization and collected on a suitable plate confirm that the 24DNT is not decomposed during the vaporization process.

The FEL tuned to 6.25 microns with 14 mJ pulses readily heated and partially vaporized the 24DNT slab (1 cm long) and 14 ms after a pulse from the laser a plume emitted is visible above the solid target. A sequence of still stroboscopic back-illuminated photos was collected in close sequence to generate a video recording the effects of the laser on the sample of 24DNT. One of the still photos is shown in FIG. 6. Some of the ejected material was collected on a neighboring substrate for further examination. Post analysis of the collected material confirmed that it had the same FTIR spectrum as the 24DNT target material. The laser energy was coupled into the 24DNT without any apparent decomposition.

Example 3

A small trace sample of RDX deposited separately on planar polyethylene and gold substrates was positioned (under ambient laboratory conditions) in line with a quantum cascade laser (QCL) beam with an output wavelength of 6.30 microns. The laser was focused to a spot size on the target of 1-2 mm$^2$. To examine any light that was emitted from the RDX sample after exposure with the QCL, an infrared camera (Photon Block 2 from FLIR, sensitive to light in the 7-12 micron range) was positioned to examine any infrared light received back from the test substrate. RDX is a common explosive in land mines and other military ordnance. The QCL allows a significant output power (>50 mW) to be achieved at the desired wavelength.

Figure 7:
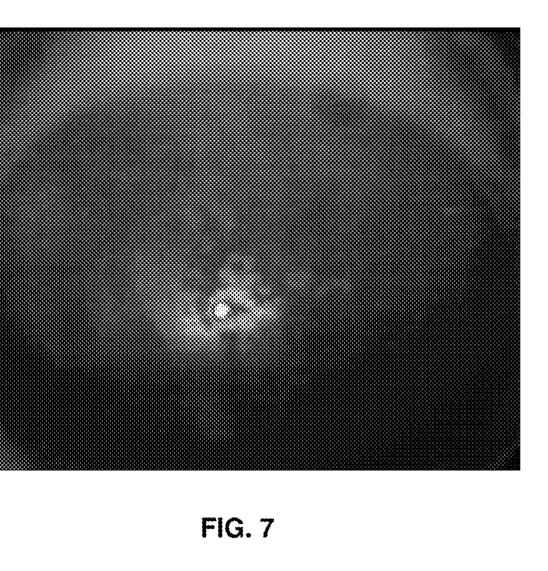
FIG. 7 is a thermal image of RDX deposited as a trace quantity on a polyethylene substrate illuminated with a QCL with incident light at 6.3 microns. The brighter area in the central part of the figure indicates the presence of the explosive.

FIG. 7 shows the thermal image of RDX deposited as a trace quantity on a polyethylene substrate, illumination with QCL at 6.3 microns (5 mW/mm$^2$). Immediately after directing the laser beam onto the RDX target, infrared light was detected indicating that the sample was being heated. When using a polyethylene substrate, the RDX heating was visible even in the background of reflected light or other emitted light. In photos taken of the sample (where black is low intensity and white is high intensity), the regions of the substrate where RDX was present appeared lighter when they were heated due to the resonant absorption of the QCL beam. Regions of the substrate where there was no RDX remained dark, indicating ambient temperature. When the laser was off, the entire region of the image was dark. Rapid RDX heating at 1 foot of stand off is clearly seen.

Figure 8:
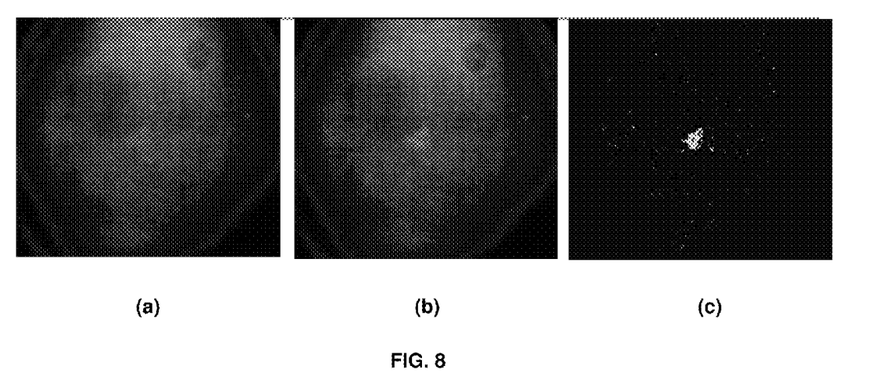

For the gold mirror substrate, the thermal conduction away from the RDX sample is higher. It is possible to see the thermal heating by inspection of the raw collected infrared image, but it was not as clear as the image collected on the polyethylene substrate. To enhance the image, a sequence of video frames was collected and a differential image was computed by subtracting the image directly before turning on the QCL with frames after turning on the QCL. Using this differential imaging approach, much clearer thermal image pictures were obtained to identify where the RDX was located, as shown in FIG. 8.

The above experiment was repeated with the same RDX deposited polyethylene target sample but the RDX was illuminated with a defocused spot size of 100 mm$^2$. The results of this experiment showed that the explosives were visible over a footprint range of a square centimeter.

By traversing or rastering the laser over the RDX deposited surface, the RDX could be mapped out over the entire surface examined. The QCL light at 6.3 microns efficiently coupled into the RDX sample and thermally heated the sample by a few degrees, which was sufficient to generate IR light from the RDX. The thermal image was captured with an uncooled microbolometer array IR detector (FLIR Photon Block II). The thermal heating of the RDX sample was very rapid and occurred within the time frame of the IR video used. At 30 frames/s, this indicates that significant thermal heating occurred in <30 ms. Cooling after the laser exposure ends may occur over a longer time period. The cooling rates for the RDX (and other analytes) can aid in identifying the trace explosive material.

Example 4

Figure 9:
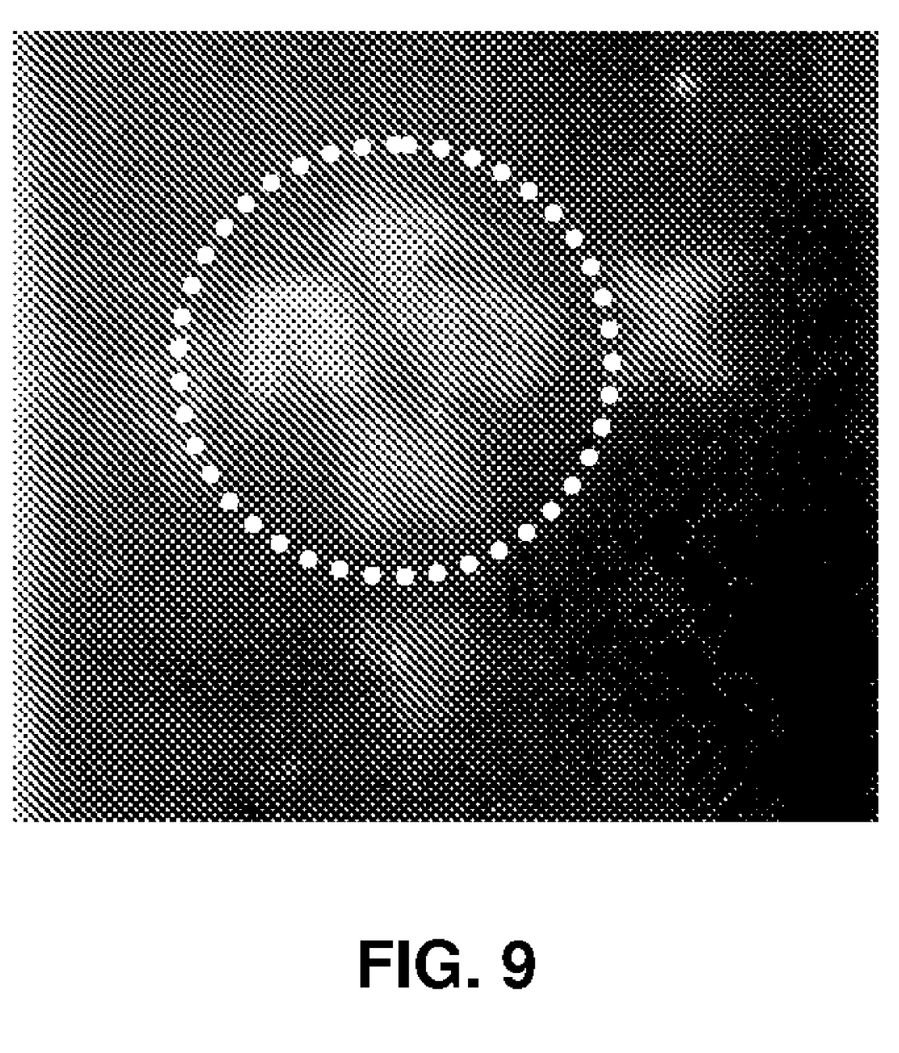
FIG. 9 shows an image of a transparent plastic substrate with RDX and TNT deposited as the horizontal and vertical letters RDX and TNT respectively and illuminated by a heat-gun but not with a laser.
Figure 10:
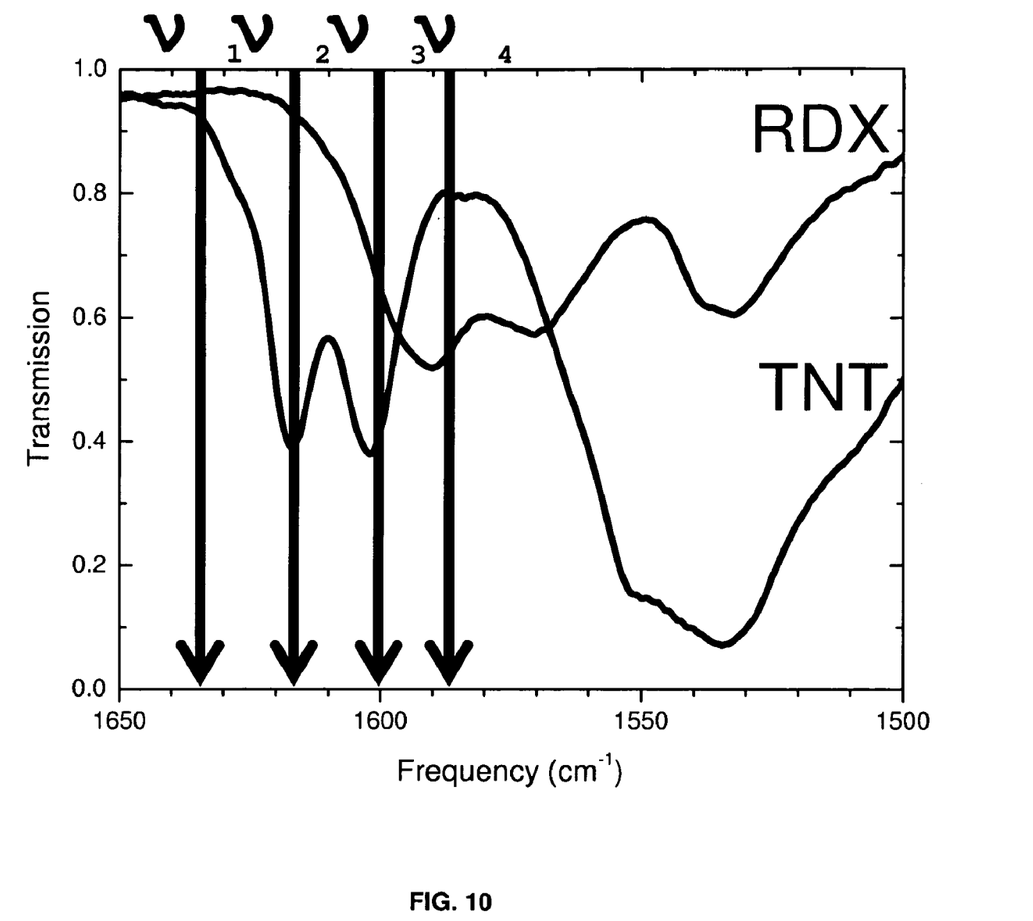
FIG. 10 shows IR transmission spectra of RDX and TNT highlighting the frequencies used in Example 4.
Figure 11:
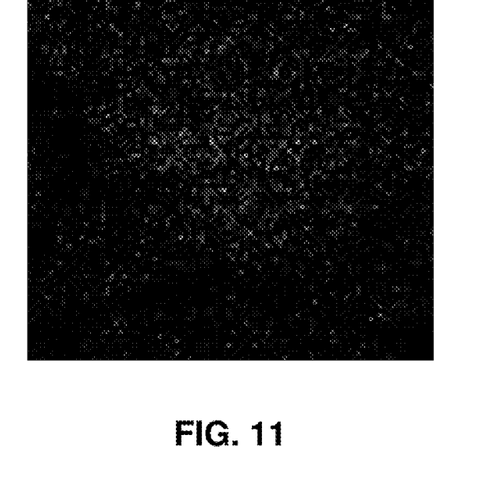
FIG. 11 shows an image of a transparent plastic substrate with RDX and TNT deposited as the horizontal and vertical letters RDX and TNT respectively and illuminated by a laser at a wavelength not selective or absorbed for either RDX or TNT.
Figure 12:
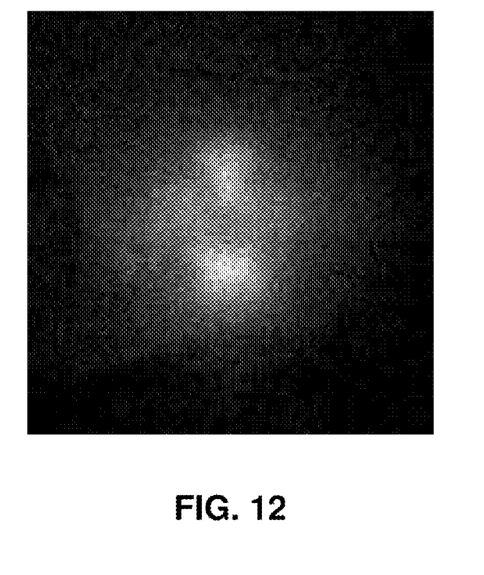
FIG. 12 shows an image of a transparent plastic substrate with RDX and TNT deposited as the horizontal and vertical letters RDX and TNT respectively and illuminated by a laser at a wavelength resonant to the TNT structure.
Figure 13:
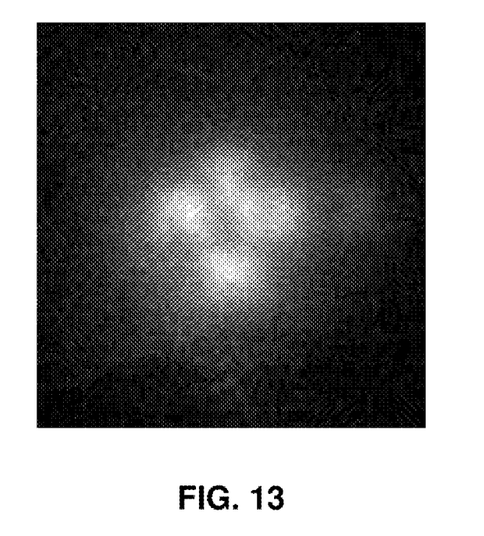
FIG. 13 shows an image of a transparent plastic substrate with RDX and TNT deposited as the horizontal and vertical letters RDX and TNT respectively and illuminated by a laser at a wavelength absorbed significantly to both the RDX and TNT structures.
Figure 14:
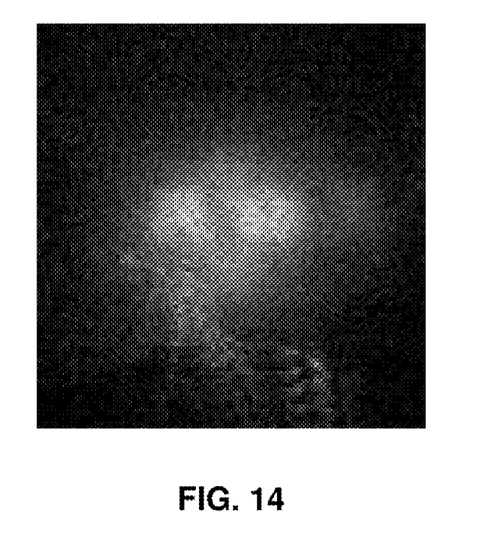
FIG. 14 shows an image of a transparent plastic substrate with RDX and TNT deposited as the horizontal and vertical letters RDX and TNT respectively and illuminated by a laser at a wavelength resonant to the RDX structure.

Selectivity was tested for a dual analyte sample containing RDX and TNT. RDX was put horizontally on a transparent plastic substrate in the form of the letters R, D, and X. Similarly, TNT was put vertically on the same stainless steel surface in the form of the letters T, N, and T. FIG. 9 shows the sample illuminated by a heatgun with no laser. FIG. 10 shows the frequencies that were used in the example: $v_1$ was off-resonance for both TNT and RDX, $v_2$ was on-resonance for TNT but not RDX, $v_3$ was on-resonance for both RDX and TNT, and $v_4$ was on-resonance for RDX but not TNT. As shown in FIG. 11, no image appeared when the laser was off-resonance. When on-resonance for TNT but not RDX, only the TNT letters were significantly visible (FIG. 12). When on-resonance for both RDX and TNT, both TNT and RDX letters were visible (FIG. 13). Finally, when on-resonance for RDX but not TNT, only the RDX letters were significantly visible (FIG. 14). The circles in the figures indicate the laser spot size.

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," are not to be construed as limiting the element to the singular.

What is claimed as new and desired to be protected by Letters Patent of the United States is:

1. A method for non-contact chemical detection, comprising:
   (a) selectively exciting one or more analytes of interest using an IR source tuned to at least one specific absorption band without decomposing more than five percent of the analyte; and
   (b) determining if the analyte is present by comparing emitted photons with an IR detector signal collected before and during or shortly after exciting the analyte, wherein a differential signal is created by subtracting a first signal taken before exciting the analyte from a second signal taken during or shortly after exciting the analyte and scaling by the power of the excitation IR source, wherein the differential signal is used to identify the presence of the analyte.

2. The method of claim 1, wherein the method is eye-safe, and wherein the method does not cause significant damage to a surface on which the analyte is located.

3. The method of claim 1, wherein the method is stand off.

4. The method of claim 1, wherein the analyte of interest is selected from the group consisting of explosives, additives to explosives, drugs, chemical warfare agents, biochemicals, and biological warfare agents.

5. The method of claim 1, wherein the IR source is a pulsed laser, continuous laser, broad band light source, filtered broad band light source, swept source, chirped source, variable source, or tunable source.

6. The method of claim 1, wherein multiple IR wavelengths are used to detect multiple analytes of interest.

7. The method of claim 1, wherein multiple IR wavelengths are used to improve selectivity where at least one IR wavelength is on-resonance for the analyte and at least one IR wavelength is off-resonance.

8. The method of claim 1, wherein the IR source emits somewhere in the range between 1 and 20 microns.

9. The method of claim 1, wherein to detect nitrogen based explosives, the IR source is tuned to a wavelength at or near a peak in the absorption spectrum characteristic of an N—O bond; wherein to detect phosphonate ester chemical warfare agents, the IR source is tuned to a wavelength at or near a peak in the absorption spectrum characteristic of a P=O double bond or a C—O—P bond; and wherein to detect drugs of abuse, the IR source is tuned to a wavelength at or near a peak in the absorption spectrum characteristic of a secondary or tertiary amine.

10. The method of claim 1, wherein the IR detector is a single channel or a multi channel detector.

11. The method of claim 1, wherein the IR detector signal in step (b) is filtered to be selective for the analyte by using an optical filter that passes wavelengths which the analyte emits and blocks wavelengths from the rest of the thermal band.

12. A method for non-contact chemical detection, comprising selectively exciting one or more analytes of interest using an IR source tuned to at least one specific absorption band without decomposing more than five percent of the analyte, wherein the analyte is excited sufficiently to generate a vapor plume, wherein the plume is examined to detect the presence of the analyte, wherein a differential signal is created by subtracting a first signal taken before exciting the analyte from a second signal taken during or shortly after exciting the analyte and scaling by the power of the excitation IR source, wherein the differential signal is used to identify the presence of the analyte.

13. The method of claim 12, wherein the method is eye-safe, and wherein the method does not cause significant damage to a surface on which the analyte is located.

14. The method of claim 12, wherein the method is stand off.

15. The method of claim 12, wherein the analyte of interest is selected from the group consisting of explosives, additives to explosives, drugs, chemical warfare agents, biochemicals, and biological warfare agents.

16. The method of claim 12, wherein the IR source is a pulsed laser, continuous laser, broad band light source, filtered broad band light source, swept source, chirped source, variable source, or tunable source.

17. The method of claim 12, wherein multiple IR wavelengths are used to detect multiple analytes of interest.

18. The method of claim 12, wherein multiple IR wavelengths are used to improve selectivity where at least one IR wavelength is on-resonance for the analyte and at least one IR wavelength is off-resonance.

19. The method of claim 12, wherein the IR source emits somewhere in the range between 1 and 20 microns.

20. The method of claim 12, wherein to detect nitrogen based explosives, the IR source is tuned to a wavelength at or near a peak in the absorption spectrum characteristic of an N—O bond; wherein to detect phosphonate ester chemical warfare agents, the IR source is tuned to a wavelength at or near a peak in the absorption spectrum characteristic of a P=O double bond or a C—O—P bond; and wherein to detect drugs of abuse, the IR source is tuned to a wavelength at or near a peak in the absorption spectrum characteristic of a secondary or tertiary amine.

21. The method of claim 12, wherein an optical technique is used to examine the vapor plume.

22. The method of claim 12, wherein the vapor plume is examined using an IR source, visible source, IR detector, visible detector, diffraction grating, filter wheel, Michelson interferometer, laser cavity and integrating sphere, or any combination thereof; and wherein the presence of the analyte is determined by using IR absorption, IR backscattering, IR thermal luminescence, Raman spectroscopy, LIBS, or any combination thereof.

23. The method of claim 12, wherein the vapor plume is examined by ion mobility spectrometry, mass spectrometry, gas chromatography, chemiluminescence, surface acoustic wave, gravimetric, microbalance, crystal resonance, or any combination thereof.

24. A system for non-contact chemical detection, comprising:
   (a) an IR source tuned to at least one specific absorption band specific to one or more analytes of interest; and
   (b) an IR detector;
   wherein the analyte is selectively excited using the IR source without decomposing more than five percent of the analyte, and the presence of the analyte is determined by comparing emitted photons with an IR detector signal collected before and during or shortly after exciting the analyte, and
   wherein a differential signal is created by subtracting a first thermal signal from a second thermal signal and scaling by the power of the excitation IR source, wherein the differential signal is used to identify the presence of the analyte.

25. The system of claim 24, wherein the detection is eye-safe, and wherein the detection does not cause significant damage to a surface on which the analyte is located.

26. The system of claim 24, wherein the detection is stand off.

27. The system of claim 24, wherein the analyte of interest is selected from the group consisting of explosives, additives to explosives, drugs, chemical warfare agents, biochemicals, and biological warfare agents.

28. The system of claim 24, wherein the IR source is a pulsed laser, continuous laser, broad band light source, filtered broad band light source, swept source, chirped source, variable source, or tunable source.

29. The system of claim 24, wherein multiple IR wavelengths are used to detect multiple analytes of interest.

30. The system of claim 24, wherein multiple IR wavelengths are used to improve selectivity where at least one IR wavelength is on-resonance for the analyte and at least one IR wavelength is off-resonance.

31. The system of claim 24, wherein the IR source emits somewhere in the range between 1 and 20 microns.

32. The system of claim 24, wherein to detect nitrogen based explosives, the IR source is tuned to a wavelength at or near a peak in the absorption spectrum characteristic of an N—O bond; wherein to detect phosphonate ester chemical warfare agents, the IR source is tuned to a wavelength at or near a peak in the absorption spectrum characteristic of a P=O double bond or a C—O—P bond; and wherein to detect drugs of abuse, the IR source is tuned to a wavelength at or near a peak in the absorption spectrum characteristic of a secondary or tertiary amine.

33. The system of claim 24, wherein the IR detector is a single channel detector or a multi channel.

34. The system of claim 24, wherein an optical filter that passes wavelengths which the analyte emits and blocks wavelengths from the rest of the thermal band is used with the IR detector.

35. A system for non-contact chemical detection, comprising:
(a) an IR source tuned to at least one specific absorption band specific to one or more analytes of interest; and
(b) means for detecting the presence of the analyte;
wherein, the analyte is selectively excited using the IR source creating a vapor plume without decomposing more than five percent of the analyte, and the presence of the analyte is determined by examining the vapor plume, wherein a differential signal is created by subtracting a first signal from a second signal and scaling by the power of the excitation IR source, wherein the differential signal is used to identify the presence of the analyte.

36. The system of claim 35, wherein the detection is eye-safe, and wherein the detection does not cause significant damage to a surface on which the analyte is located.

37. The system of claim 35, wherein the detection is stand off.

38. The system of claim 35, wherein the analyte of interest is selected from the group consisting of explosives, additives to explosives, drugs, chemical warfare agents, biochemicals, and biological warfare agents.

39. The system of claim 35, wherein the IR source is a pulsed laser, continuous laser, broad band light source, filtered broad band light source, swept source, chirped source, variable source, or tunable source.

40. The system of claim 35, wherein multiple IR wavelengths are used to detect multiple analytes of interest.

41. The system of claim 35, wherein multiple IR wavelengths are used to improve selectivity where at least one IR wavelength is on-resonance for the analyte and at least one IR wavelength is off-resonance.

42. The system of claim 35, wherein the IR source emits somewhere in the range between 1 and 20 microns.

43. The system of claim 35, wherein to detect nitrogen based explosives, the IR source is tuned to a wavelength at or near a peak in the absorption spectrum characteristic of an N—O bond; wherein to detect phosphonate ester chemical warfare agents, the IR source is tuned to a wavelength at or near a peak in the absorption spectrum characteristic of a P=O double bond or a C—O—P bond; and wherein to detect drugs of abuse, the IR source is tuned to a wavelength at or near a peak in the absorption spectrum characteristic of a secondary or tertiary amine.

44. The system of claim 35, wherein an optical technique is used to examine the vapor plume.

45. The system of claim 35, wherein the vapor plume is examined using an IR source, visible source, IR detector, visible detector, diffraction grating, filter wheel, Michelson interferometer, laser cavity and integrating sphere, or any combination thereof; and wherein the presence of the analyte is determined by using IR absorption, IR backscattering, IR thermal luminescence, Raman spectroscopy, LIBS, or any combination thereof.

46. The system of claim 35, wherein the vapor plume is examined by ion mobility spectrometry, mass spectrometry, gas chromatography, chemiluminescence, surface acoustic wave, gravimetric, microbalance, crystal resonance, or any combination thereof.

* * * * *